(12) United States Patent
Curbera et al.

(10) Patent No.: US 10,411,895 B2
(45) Date of Patent: Sep. 10, 2019

(54) CREATING MATCH COHORTS AND EXCHANGING PROTECTED DATA USING BLOCKCHAIN

(71) Applicant: International Business Machines Corporation, Armonk, NY (US)

(72) Inventors: Francisco P. Curbera, Hastings On Hudson, NY (US); Yurdaer N. Doganata, Chestnut Ridge, NY (US); Maria Eleftheriou, Mt Kisco, NY (US); Mark H. Overman, Dedham, MA (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 15/586,393

(22) Filed: May 4, 2017

(65) Prior Publication Data
US 2018/0323975 A1 Nov. 8, 2018

(51) Int. Cl.
*H04L 29/06* (2006.01)
*H04L 9/32* (2006.01)
(Continued)

(52) U.S. Cl.
CPC .......... *H04L 9/3236* (2013.01); *G06F 21/602* (2013.01); *G16H 10/60* (2018.01);
(Continued)

(58) Field of Classification Search
None
See application file for complete search history.

(56) References Cited

U.S. PATENT DOCUMENTS 10,114,969 B1 * 10/2018 Chaney .............. G06F 21/6218
2015/0149208 A1    5/2015 Lynch et al.
(Continued)

FOREIGN PATENT DOCUMENTS

WO    2016168922 A1    10/2016

OTHER PUBLICATIONS

Computer Desktop Encyclopedia definition of "processor". http://lookup.connputerlanguage.com/host_app/search?cid=C999999&term=processor&lookup.x=0&lookup.y=0 (Year: 2014).*
(Continued)

*Primary Examiner* — Jeremiah L Avery
(74) *Attorney, Agent, or Firm* — Ingrid M. Foerster; SVL IPLaw (57) ABSTRACT

A method, computing system and computer program product are provided. A first entity system that stores sensitive information associated with different entities applies a hash function a portion of the sensitive information to produce hash values. Transaction information pertaining to transactions performed on entity systems are stored within a blockchain database accessible to the entity systems. The transaction information includes hash values corresponding to associated entities from the entity systems. The hash values of the first entity system are compared to the hash values from others of the entity systems to determine entity systems containing information pertaining to same entities. The sensitive information for an entity of the first entity system is exchanged with the determined entity systems containing information for that entity.

21 Claims, 7 Drawing Sheets

(51) Int. Cl.
*G16H 10/60* (2018.01)
*G06F 21/60* (2013.01)

(52) U.S. Cl.
CPC ........ *H04L 9/3239* (2013.01); *H04L 63/0428* (2013.01); *H04L 63/20* (2013.01); *H04L 2209/38* (2013.01); *H04L 2209/88* (2013.01)

(56) References Cited

U.S. PATENT DOCUMENTS

| | | | |
|---|---|---|---|
| 2015/0332283 A1 | 11/2015 | Witchey | |
| 2016/0226840 A1 | 8/2016 | Buccella et al. | |
| 2017/0048216 A1* | 2/2017 | Chow | G06Q 20/0655 |
| 2017/0109475 A1* | 4/2017 | Kaditz | G16H 10/60 |
| 2017/0169250 A1* | 6/2017 | White | G06F 21/602 |
| 2017/0250972 A1* | 8/2017 | Ronda | H04L 9/08 |
| 2017/0286717 A1* | 10/2017 | Khi | H04L 63/06 |
| 2017/0289111 A1* | 10/2017 | Voell | H04L 9/3236 |
| 2017/0317997 A1* | 11/2017 | Smith | H04L 9/0861 |
| 2018/0013567 A1* | 1/2018 | Davis | H04L 9/0637 |
| 2018/0068130 A1* | 3/2018 | Chan | G06F 21/6227 |
| 2018/0089436 A1* | 3/2018 | Smith | G06F 21/575 |
| 2018/0109541 A1* | 4/2018 | Gleichauf | H04L 63/123 |
| 2018/0130050 A1* | 5/2018 | Taylor | G06Q 20/3674 |
| 2018/0248845 A1* | 8/2018 | Irwan | H04L 9/3239 |

OTHER PUBLICATIONS

Kishigami, Jay et al. The Blockchain-based Digitial Content Distribution System. 2015 IEEE Fifth International Conference on Big Data and Cloud Computing. https://ieeexplore.ieee.org/stamp/stamp.jsp?tp=&arnumber=7310737 (Year: 2015).*

Fu, Dongqi; Fang, Liri. Blockchain-based Trusted Computing in Social Network. 2016 2nd IEEE International Conference on Computer and Communications (ICCC). https://ieeexplore.ieee.org/stamp/stamp.jsp?tp=&arnumber=7924656 (Year: 2016).*

"Integrating the Healthcare Enterprise (IHE)", IHE Wiki, http://wiki.ihe.net/index.php/Main_Page, retrieved from Internet Jan. 2017, 2 pages.

PCT International Search Report and Written Opinion dated Mar. 28, 2018, PCT/EP2017/083282, 12 pages.

* cited by examiner

CREATING MATCH COHORTS AND EXCHANGING PROTECTED DATA USING BLOCKCHAIN

BACKGROUND

Field of the Invention

Present invention embodiments are related to systems, methods and computer program products for determining a match-cohort or overlap of data pertaining to entities associated with data items stored in multiple entity systems without exposing any information regarding the associated entities, securely exchanging sensitive data related only to the determined match-cohort, and coordinating, among the multiple entity systems, communications with the associated entities based on a stored set of rules.

Discussion of Related Art

Healthcare entities store different components of patient data. Some healthcare entities desire to offer enhanced services by merging or analyzing their patient data with patient data from one or more other healthcare entities. Each healthcare entity serves a patient population (cohort) and some portion of the patient populations may be served by multiple healthcare entities. This portion of the patient populations that is identified as common between at least two healthcare entities is called a match-cohort. As an example, a pharmacy benefit manager (PBM) manages medication data of 400,000 patients and a healthcare provider manages medical data and office visit data of 40,000 patients. The size of an overlapping population (i.e., a match-cohort) is unknown and, in existing healthcare entity systems, can only be determined by exchanging protected healthcare information (PHI).

In order to find the match-cohort with minimal exposure of the PHI, a healthcare entity system of the healthcare provider, which has information regarding a smaller number of patients than a healthcare entity system of the PBM, shares certain patient information such as, for example, date of birth, social security number, last name, first name and gender, with the healthcare entity system of the PBM. In this way, existing healthcare entity systems expose only a minimal amount of the PHI. Before any patient information is shared, the healthcare provider and the PBM typically enter into one or more written agreements to permit the sharing of data and comply with regulations involving the secure handling of PHI. These types of agreements can include a confidentiality agreement, a data sharing agreement, a business associate agreement (BAA), a data security agreement, and/or a collaboration agreement. In addition, most healthcare entities require a healthcare entity receiving PHI to complete a data security review such that the healthcare entity receiving the PHI must provide evidence that their healthcare entity system meets minimum security requirements.

After the healthcare entity system of the PBM receives the certain patient information from the healthcare entity system of the healthcare provider, the healthcare entity system of the PBM compiles a master list of, for example, 25,000 patients in the match-cohort population using master data management technologies.

Another known method for two entities to create a match-cohort is for the two entities to use services of an independent third entity who would receive the certain medical data from the entity systems of the two entities. However, multiple agreements are to be agreed to among the three entities and several security reviews are to be conducted before any sensitive data is shared.

As patient populations served by the different healthcare entities change due to patient drop outs and new patient onboarding, the process described above for determining a match-cohort is repeated periodically.

At times, a healthcare entity that shares match-cohort patient data with one or more other healthcare entities may wish to communicate with a match-cohort patient to positively affect patient behavior and/or prevent over-communication. The healthcare entities may wish to coordinate their communications with the match-cohort patient to positively affect patient behavior and/or prevent over-communication. Effective communication is dependent on knowing the communication history of all of the healthcare entities with the patient. Existing healthcare entity systems do not provide a way to coordinate activities, such as communications, with match-cohort patients.

A blockchain database is a type of distributed ledger, which has a network of replicated databases, each of which is synchronized and visible to anyone within the network. Blockchain networks can be either private or public. Carried out digital transactions are grouped together by blockchain in a cryptographically protected block with other transactions that have occurred and were sent out to the entire network within a preceding 10 minutes. Members in the network with high levels of computing power (miners) compete with each other to validate the transactions by solving complex coded problems. A first miner to solve the problems and validate the block receives a reward. The validated block of transactions is timestamped and added to a chain of blocks in a linear, chronological order. Newly validated blocks are linked to older blocks. The chain of transactions show every transaction performed in a history of the chain. This is a blockchain transaction ledger, which is also known as a blockchain database. The transaction ledger is continually updated and synchronized with each replicated database so that every distributed transaction ledger is identical.

U.S. Patent Application Publication No. 2015/0332283 to Witchey discloses healthcare transaction validation systems and methods. Witchey teaches one or more healthcare validation devices receiving a healthcare transaction that includes a set of healthcare tokens representing actions taken with respect to a stakeholder. A validation device determines whether the healthcare transaction satisfies validity requirements, and when the validity requirements are satisfied, the validation device updates a healthcare historical blockchain.

SUMMARY

In a first aspect of the invention, a method of exchanging sensitive data among multiple entity systems is provided. According to the method, a hash function is applied to a portion of sensitive information of a first entity system to produce hash values. Transaction information regarding transactions performed on the first entity system are stored within a blockchain database that is accessible to the multiple entity systems that have different information for at least some of the same served entities. The transaction information includes the hash values for the portion of sensitive information. The blockchain database further includes transaction information from the multiple entity systems, including hash values from others of the multiple entity systems. The hash values of the first entity system are compared to the hash values from the others of the multiple entity systems to determine entity systems containing information pertaining to the same served entities. The sensitive information for common served entities of the first entity system is exchanged with the determined entity systems containing information for those common served entities. This method has advantages over existing systems such as: determining a match-cohort for multiple entity systems without exposing any sensitive information; and determining a size of the match-cohort for the multiple entity systems. At this point, business entities corresponding to the multiple entity systems may not have any or limited business agreements with each other or conducted any or limited security reviews because no identifying information had been exchanged.

In some embodiments, the blockchain database includes encryption parameters of the determined entity systems, each of the encryption parameters for a corresponding determined entity system being associated with a private key limiting decryption to only a corresponding entity system. These embodiments have an advantage over existing systems such that only intended recipients of encrypted data have an ability to decrypt the encrypted data. Other embodiments may include, in the blockchain database, information from the entity systems pertaining to actions involving a served entity associated with the sensitive information and a set of rules specifying acceptable actions may be included in the blockchain database and may be applied to validate requested actions involving the associated served entity. These other embodiments have an advantage over existing systems because various actions involving an associated served entity can be coordinated among the entity systems.

Other aspects of the invention include a first entity system that is configured to perform the above-mentioned methods and a computer program product having computer readable program code embodied therewith to be executed by at least one processor to perform the above-mentioned methods.

BRIEF DESCRIPTION OF THE DRAWINGS

Generally, like reference numerals in the various figures are utilized to designate like components.

DETAILED DESCRIPTION

Present invention embodiments include methods, systems and computer program products for determining a match-cohort with respect to served entity data items stored in multiple entity systems. In various embodiments, each of the entity systems may apply a same hash function to a portion of sensitive information included in each served entity data item to produce respective hash values. Each of the entity systems may then broadcast its produced hash values. Because a hash function produces a hash value that cannot be transformed back to an original value, no sensitive information is exposed when the hash values are broadcast. Further, business agreements and/or security reviews may not be needed before the hash values are broadcast. Each respective entity system stores transaction information pertaining to transactions performed by the respective entity system in a blockchain database (i.e., a blockchain ledger), which is accessible to the multiple entity systems. The transaction information may include respective hash values transmitted by each of the entity systems.

A first entity system of the multiple entity systems may compare the respective hash values in the blockchain database from other entity systems of the multiple entity systems with its own produced hash values in order to determine which of the other entity systems include information pertaining to served entities associated with served entity data items of the first entity system (i.e., a match-cohort). A business entity using the first entity system and one or more second business entities using one or more second entity systems of the determined other entity systems may agree to various business agreements and may conduct security reviews before any served entity data items are exchanged between the first entity system and the one or more second entity systems. The first entity system may then exchange respective match-cohort served entity data items with each of the one or more second entity systems. The exchanged match-cohort served entity data items may be encrypted such that only a single intended recipient second entity system has a key to decrypt the encrypted exchanged data items. Thus, if the first entity system is to exchange match-cohort served entity data items with, for example, three second entity systems, the first entity system would encrypt the match-cohort served entity data items for a first of the second entity systems and broadcast the encrypted match-cohort served entity data items, then encrypt the match-cohort served entity data items for a second of the second entity systems and broadcast the encrypted match-cohort entity served data items, and finally encrypt the match-cohort served entity data items for a third of the second entity systems and broadcast the encrypted match-cohort served entity data items.

In some embodiments, a set of rules may be accessible to each of the multiple entity systems. The set of rules may be stored in the blockchain database. The set of rules may include a set of conditions that are to exist before any of the multiple entities that share match-cohort served entity data items are given permission to communicate with a served entity associated with any of the match-cohort served entity data items. For example, a set of rules may permit a communication with the served entity associated with any of the match-cohort served entity data items only when none of the multiple entity systems permitted a communication with the served entity within a preceding predetermined time period. The preceding predetermined time period may be two weeks, one month, or another suitable time period. By coordinating communications in this manner, the served entities associated with the match-cohort served entity data items will not be overwhelmed by too many communications occurring over the preceding predetermined time period.

Figure 1:
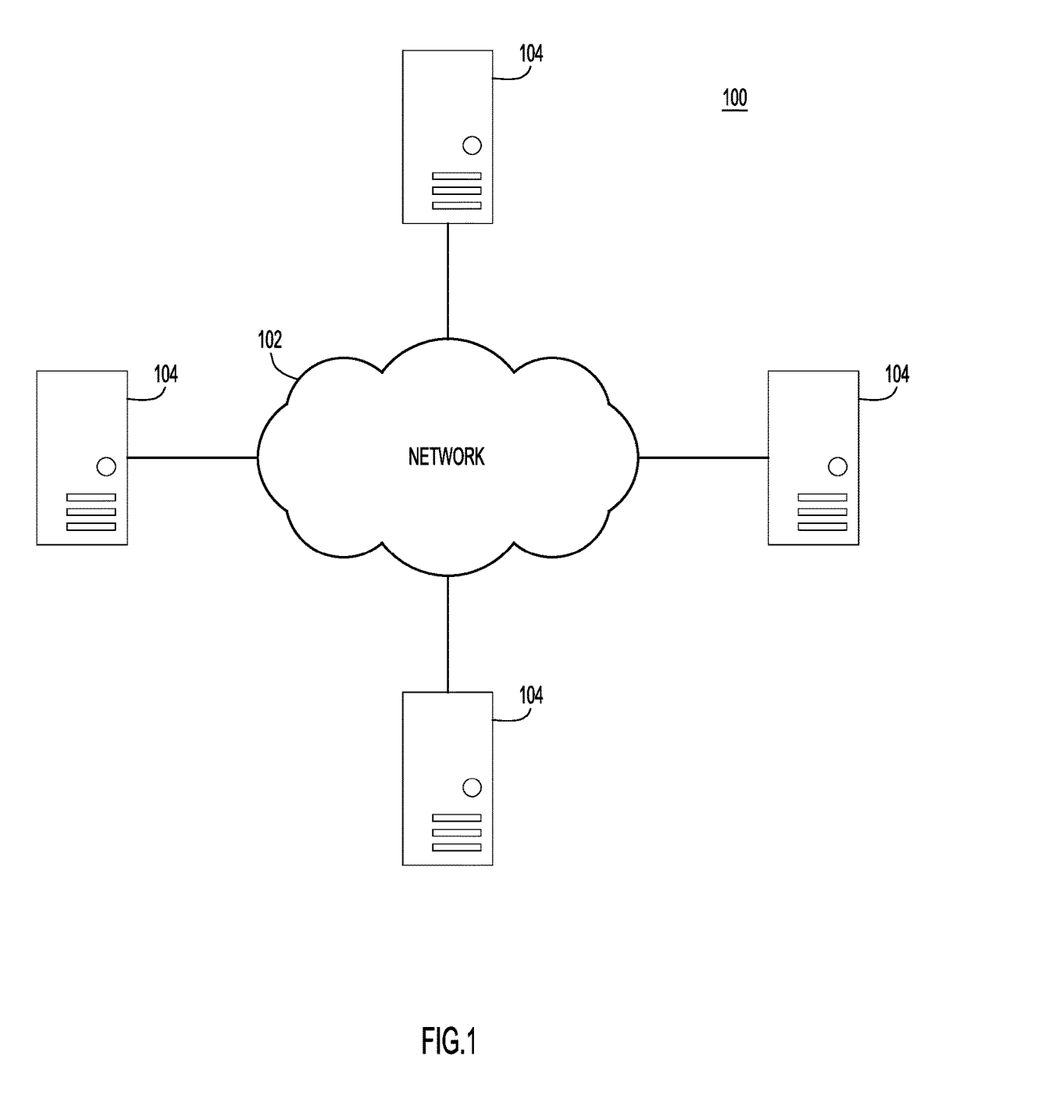
FIG. 1 illustrates an example environment in which various embodiments may be implemented.

FIG. 1 shows an example environment 100 in which various embodiments may be implemented. Example environment 100 may include a network 102 and a number of entity systems 104 connected to network 102. Network 102 may include a local area network (LAN), a wide area network (WAN), a public switched data network (PSDN), the Internet, an intranet, other types of networks, or any combination of the above. Entity systems 104 may have access to a database management system (not shown), which may be local or remote with respect to entity systems 104. Further, in some embodiments, some of entity systems 104 may include a server or a group of servers such as a server farm. Entity systems 104 may communicate with each other via network 102.

Figure 2:
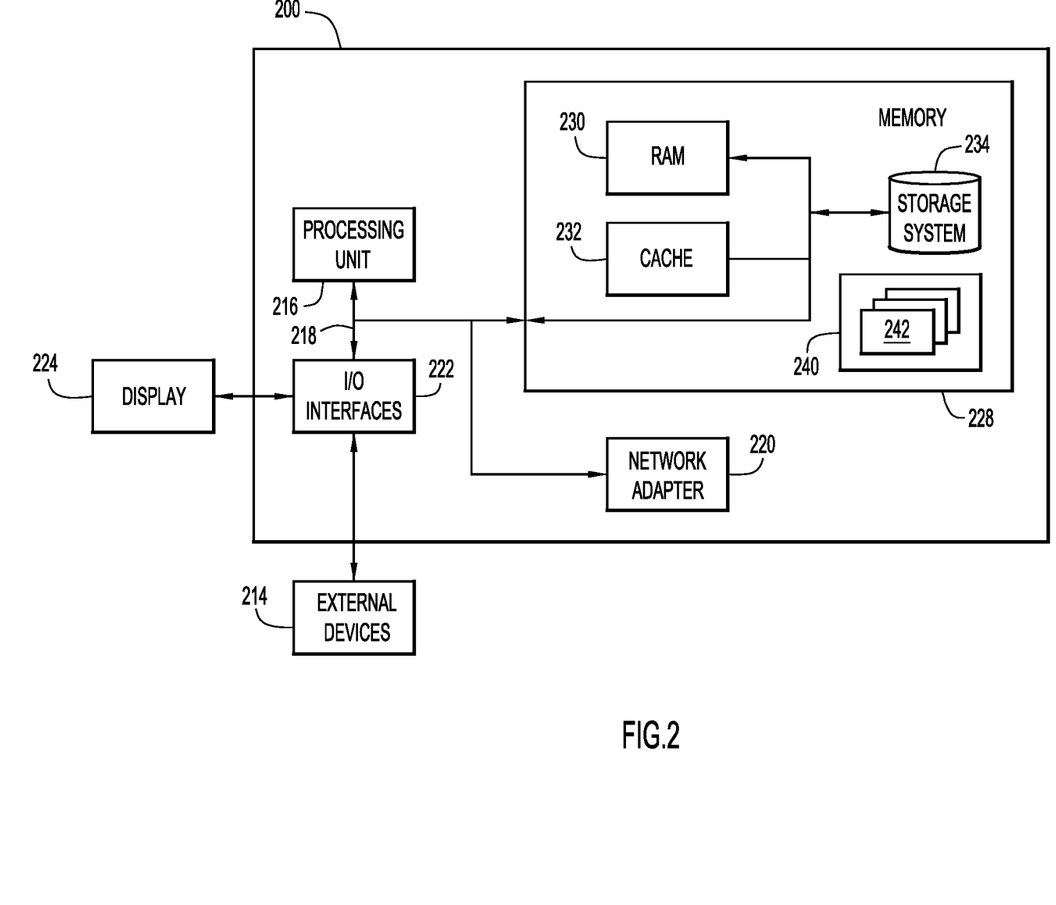
FIG. 2 illustrates an example computer system that may implement entity systems according to various embodiments.

Each entity system 104 may each be implemented by at least one computing system 200 shown in FIG. 2. Computing system 200 is shown in a form of a general-purpose computing device. Components of computing system 200 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, a display 224, etc.; one or more devices that enable a user to interact with computing system 200; and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

Figure 6:
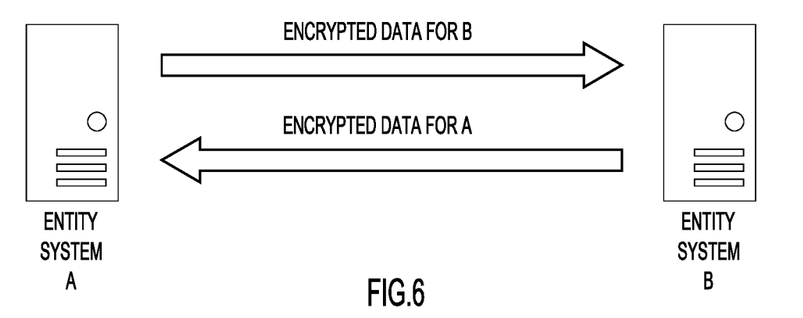
FIG. 6 shows two entity systems broadcasting their respective sensitive data encrypted by using the encryption parameters of an intended entity system according to an embodiment of the present invention.
Figure 7:
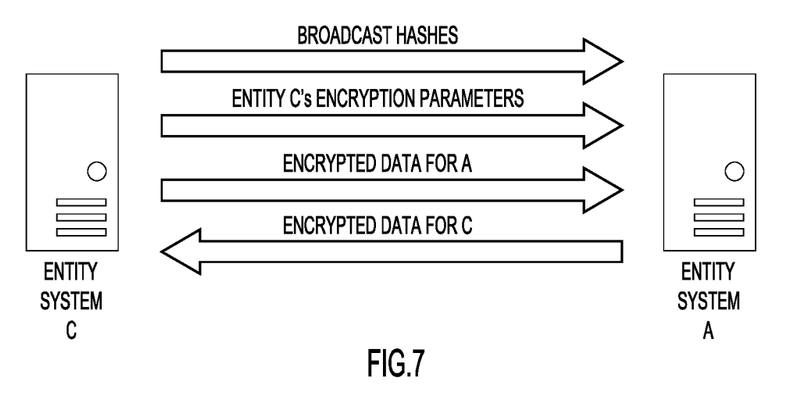
FIG. 7 illustrates an example process by which two entity systems can exchange sensitive data with each other when one of the two entity systems comes online after a second of the two entity systems has already determined a match-cohort with respect to one or more other entity systems according to an embodiment of the present invention.
Figure 8:
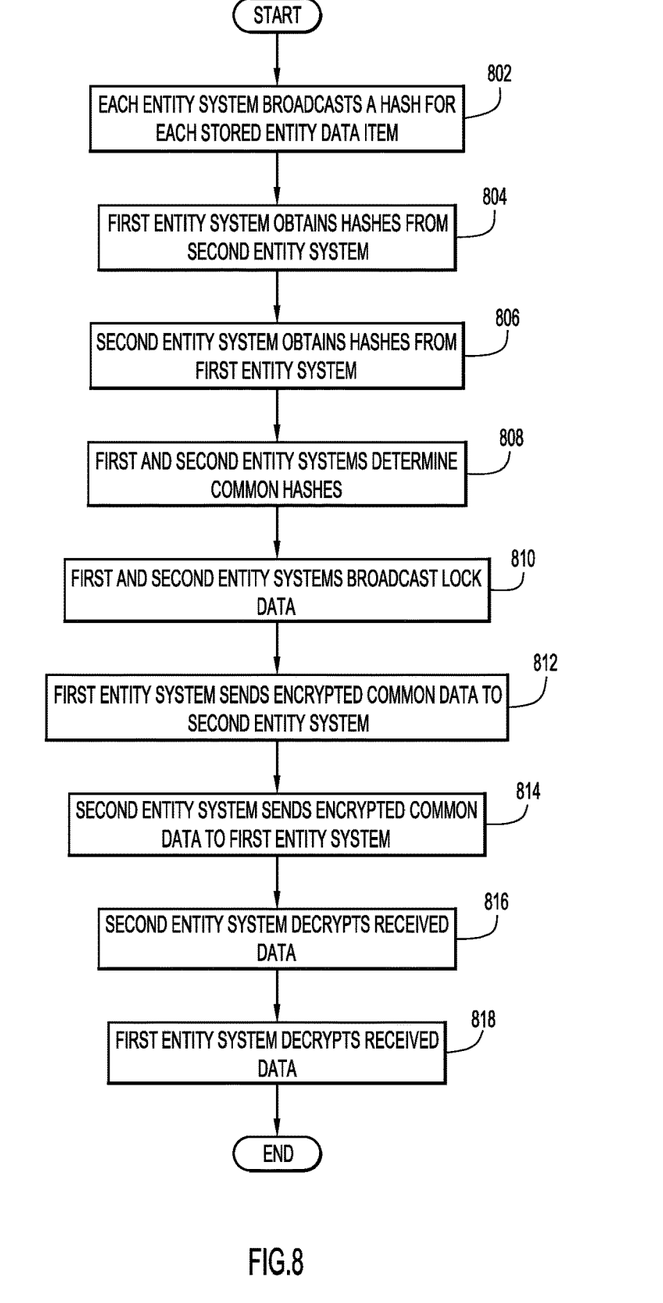
FIG. 8 is a flowchart illustrating an example process by which two entity systems can determine a match-cohort, exchange sensitive encrypted data that can only be decrypted by an intended recipient entity system, and decrypt the encrypted sensitive data according to an embodiment of the present invention.

FIG. 8 is a flowchart that, along with FIGS. 3-7, illustrate example processing that may be performed by first entity system in various embodiments. The process may begin with each respective entity system performing a same hash function on a portion of each served entity data item of the respective entity system to produce respective hash values, which may be stored by the respective entity system and may be broadcast to other entity systems via a network (act 802). In one embodiment, the portion of each served data item may include a social security number, a date of birth, a gender, a last name, and a first name. Various embodiments may perform a hash function on different portions of each entity data item. A hash function is a one-way function that transforms data to produce a hash value. The hash function is not reversible. That is, original data cannot be determined from the hash value.

Each respective entity system may store transaction information regarding transactions performed by the respective entity system in a blockchain database, which is accessible by the other entity systems. Therefore, the hash values broadcast by each of the entity systems may be stored in a blockchain transaction ledger (i.e., a blockchain database).

Figure 3:
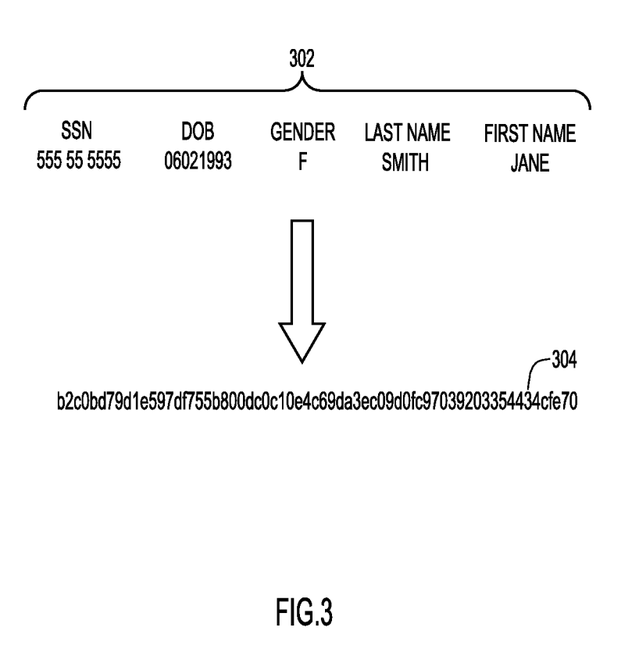
FIG. 3 shows an example in which a hash function is applied to a portion of sensitive information to produce a hash value according to an embodiment of the present invention.

FIG. 3 shows a portion 302 of an example served entity data item that includes a social security number, a date of birth, a gender, a last name, and a first name. The hash function may be performed by a first entity system on the portion of each entity data item to produce respective hash values. FIG. 3 shows an example hash value 304 produced by applying the hash function to the served entity data item 302. One embodiment, uses a SHA-256 algorithm to produce an almost-unique, fixed size, 256-bit (32-byte) hash value. Other embodiments may employ other hash functions.

Figure 4:
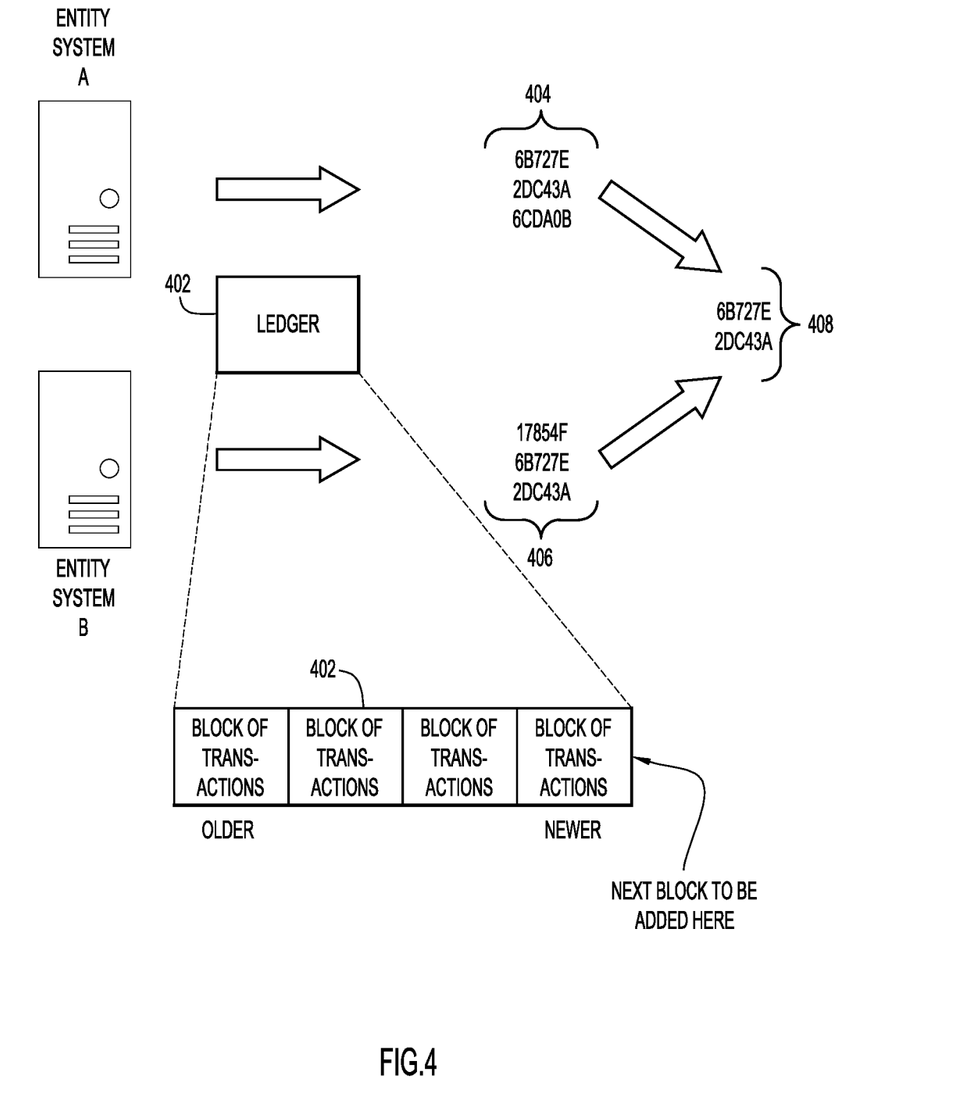
FIG. 4 illustrates an example process in which two entity systems broadcast their respective hash values produced from a portion of sensitive information of each of the two entity systems and determine a match-cohort by finding hash values common to the two entity systems according to an embodiment of the present invention.

FIG. 4 shows two entity systems, entity system A and entity system B, broadcasting their respective hash values 404, 406 which are recorded in a transaction ledger 402 (i.e., a blockchain database), accessible by other entity systems. As previously mentioned, validated transactions are recorded in transaction ledger 402 in timestamped blocks and newer timestamped blocks are linked to older timestamped blocks.

Returning to FIG. 8, a first entity system obtains hash values produced by a second entity system (act 804) from a broadcast or from the blockchain transaction ledger and the second entity system obtains the hash values produced by the first entity system from a broadcast or from the blockchain transaction ledger (act 806). Each of the first and second entity systems may determine matching served entity data items (a match-cohort) by comparing the hash values produced by its own entity system with the hash values produced by another of the first and second entity systems (act 808). Matching hash values indicate corresponding entity data items associated with a same entity. FIG. 4 shows matching hash values 408 from entity system A's hash values 404 and entity system B's hash values 406 corresponding to served entity data items of a match-cohort.

Next, entity system A and entity system B may broadcast their respective lock data, which may be recorded in the blockchain ledger (act 810).

Figure 5:
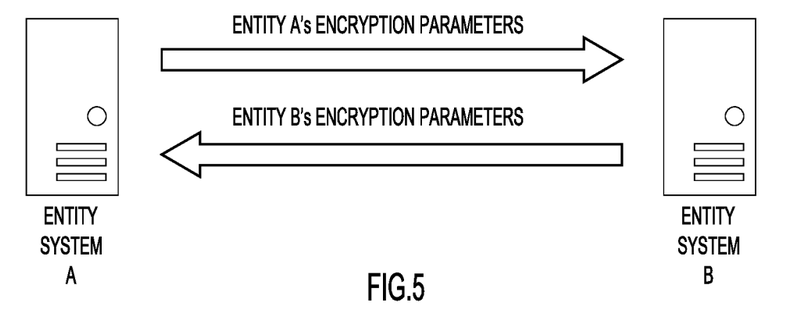
FIG. 5 illustrates two entity systems broadcasting their respective encryption parameters according to an embodiment of the present invention.

FIG. 5 shows two entity systems, entity system A and entity system B, sharing lock data (i.e., encryption parameters). The encryption parameters, or lock data, are parameters that enable an entity system to encrypt sensitive data in such a way that it can be decrypted only by an owner of the lock data. In some embodiments, the lock data may be an entity system's public key. Data encrypted using a public key, which may be known to other entity systems, can be decrypted only by using the entity system's corresponding private key, which is known only to that entity system. It is impossible to determine an entity system's private key from the entity system's public key.

As an example, entity system A may broadcast its lock data using parameters n and e, where n is a product of two random large prime numbers, such that the product n is, for instance, more than 2,000 bits long, and e is an odd exponent. Before sending sensitive data to entity system A, an entity system would encrypt the sensitive data according to Encrypted Sensitive Data=[sensitive data]$^e$mod($n$).

Only entity system A can decrypt the encrypted sensitive data using a private key associated with the lock. The private key may be related to parameters e and n, but is computationally not feasible for other entity systems to determine.

Before sending any sensitive data, the first and second entity systems may have multiple business agreements with each other and may have conducted one or more security reviews. The first entity system may then broadcast sensitive data (i.e., match-cohort served entity data items) encrypted using the second entity system's lock data and the second entity system may broadcast sensitive data encrypted (i.e., match-cohort entity served data items) using the first entity system's lock data (acts 812 and 814).

FIG. 6 shows entity system A broadcasting sensitive match-cohort served entity data items encrypted using entity system B's lock data and entity system B broadcasting sensitive match-cohort served entity data items encrypted using entity system A's lock data.

Each of the first entity system and the second entity system may decrypt the broadcast match-cohort served entity data items intended for it using a respective private key (acts 816 and 818). The broadcasted encrypted match-cohort served entity data items may be recorded in the blockchain transaction ledger such that any entity system may have access to the recorded encrypted match-cohort entity data items, but only the intended entity system recipient is able to decrypt the encrypted match-cohort served entity data items using its private key.

After exchanging and decrypting encrypted sensitive data among the entity systems, the entity systems may analyze the exchanged sensitive data to identify one or more issues triggering an action involving an entity associated with the sensitive data such as, for example, communicating with the associated entity or other action.

FIG. 7 illustrates a third entity system, entity system C, at a later point in time, broadcasting hash values produced from a portion of entity system C's served entity data items. Entity system C may wish to exchange entity data items of a match-cohort with entity system A. Entity system C may obtain hash values previously broadcast by entity system A by accessing the blockchain transaction ledger, as previously discussed, and may broadcast its hash values. A match-cohort can then be determined by entity systems A and C by comparing the hash values from the other entity system with its own hash values. As previously mentioned, matching hash values correspond to entity data items associated with a same entity. Entity system C may broadcast its lock data (i.e., encryption parameters) and may obtain entity system A's lock data from the blockchain transaction ledger and entity system A may obtain entity system C's lock data either via the broadcast of entity system C's lock data or from the blockchain transaction ledger. After obtaining the lock data, entity system A and entity system C may encrypt match-cohort served entity data items using the lock data for the respective intended entity system recipient and may broadcast its encrypted match-cohort served entity data items.

In various embodiments, when additional data is broadcast by an entity system, the determined entity systems may be updated based on the additional data being received in a new block, which is added to the blockchain transaction ledger.

In some embodiments, a set of rules may be stored in the blockchain database. As an example, a group of entity systems that share match-cohort served entity data items may wish to avoid excessive communications with served entities associated with served entity data items of the match-cohort. A rule may be recorded in the blockchain transaction ledger indicating that communication requests from entity systems that wish to communicate with a served entity associated with a match-cohort served entity data item will be honored only if none of the match-cohort entity systems have communicated with the served entity within a predetermined time period preceding the communication request. The predetermined time period may be two weeks, one month, or another suitable time period.

Although the example above concerns communications with a served entity associated with a match-cohort served entity data item, various embodiments may coordinate other types of requests among entity systems that involve a served entity associated with a match-cohort served entity data item. In this way, activities such as, for example, communications or other activities involving a served entity associated with a match-cohort served entity data item may be coordinated among entities using the entity systems.

Figure 9:
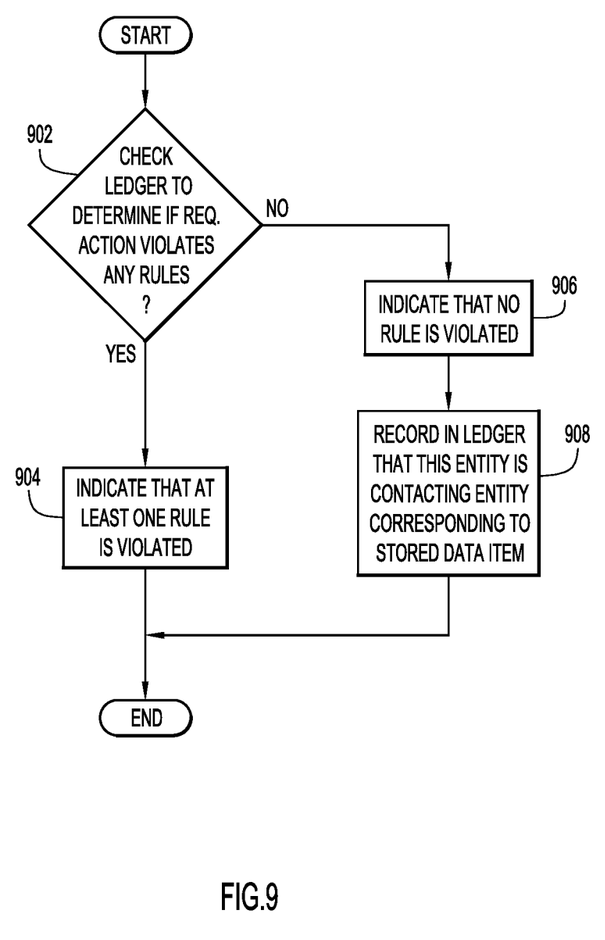
FIG. 9 is a flowchart illustrating an example process by which an entity system validates a requested action when the requested action does not violate a set of rules according to an embodiment of the present invention.

FIG. 9 is a flowchart of an example process for determining whether a set of rules would be violated by a requested action involving a served entity associated with a match-cohort served entity data item and honoring the requested action only when the set of rules would not be violated.

The process may begin with an entity system determining whether a requested action involving a served entity associated with a match-cohort served entity data item would violate any of a set of rules (act 902). In some embodiments, the requested action may be a communication request for communicating with the served entity, or another requested action involving the served entity. The entity system may access the set of rules, which may be stored in a blockchain transaction ledger and may determine whether any rule of the set of rules would be violated by examining transaction information recorded in a blockchain transaction ledger. If the requested action would violate any of the set of rules, then an indication may be provided indicating that the requested action would violate at least one rule of the set of rules (act 904) and the process may end.

If, during act 902, the entity system determines that the requested action would not violate any of the set of rules, then an indication may be provided indicating that the requested action does not violate any of the rules (act 906) and a transaction may be recorded in the block chain transaction ledger indicating that the requested action is honored (act 908).

In some embodiments, the process of FIG. 9 may be used to address privacy concerns of a patient. For example, if a patient opts out of receiving communications from business entities associated with entity systems, then the blockchain transaction ledger may be updated with a rule that prevents any further communication with that patient.

Embodiments may be used with a variety of different type of entities. As an example, some embodiments may be used with entity systems associated with healthcare, including but not limited to, doctors' offices, pharmacies, pharmacy benefit managers (PBMs), suppliers, payers, clinical knowledge authorities, regulatory agencies, and registries. In some embodiments, the served entity data items may be protected health information of served entities including patients. In other embodiments, the served entity data items may be other types of sensitive data.

Embodiments provide a number of advantages over existing systems. Some of which are:

When determining a match-cohort, only hash values of a portion of served entity data items are exchanged. Because the hash values, themselves, are not sensitive data and cannot be decrypted, no exposure of sensitive data occurs at this point and no or limited business agreements and/or security reviews are required.

Each entity system may obtain other entity system's hash values and lock data from a blockchain database, or blockchain transaction ledger. Therefore, each entity system need not be online when other entity systems broadcast their respective hash values and lock data.

Requested actions involving entities associated with match-cohort served entity data items such as, for example, a communication request regarding communicating with a served entity associated with a match-cohort served entity data item, or other requested action involving the associated served entity, may be coordinated among entity systems by honoring only requested actions that do not violate any rule of a set of rules.

Embodiments provide continuous updates of match-cohorts, and business agreements and enable an uninterrupted exchange of sensitive data by actions such as, for example, monitoring a blockchain transaction ledger.

The environment of present invention embodiments may include any number of computers or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim:

1. A method of exchanging sensitive information among a plurality of entity systems comprising:
    applying a hash function to a portion of sensitive information of a first entity system to produce hash values;
    storing transaction information pertaining to transactions performed on the first entity system within a blockchain database accessible to the plurality of entity systems, wherein the transaction information includes the hash values for the portion of sensitive information, and wherein the blockchain database includes transaction information from the plurality of entity systems including hash values from others of the plurality of entity systems;
    comparing the hash values of the first entity system to the hash values from the others of the plurality of entity systems to determine entity systems containing information pertaining to one or more common served entities; and
    exchanging the sensitive information for the one or more common served entities of the first entity system with the determined entity systems containing information for those one or more common served entities.

2. The method of claim 1, wherein the blockchain database further includes encryption parameters for encrypting data to be sent to the plurality of entity systems, and the exchanging the sensitive information comprises:
    encrypting the sensitive information for the one or more common served entities utilizing the encryption parameters of each of the determined entity systems within the blockchain database, wherein the encryption parameters for a corresponding entity system are associated with a private key limiting decryption to that corresponding entity system; and
    transmitting the encrypted sensitive information to each of the determined entity systems for decryption via the associated private key.

3. The method of claim 2, further comprising:
    analyzing the exchanged sensitive information to identify one or more issues triggering an action involving a served entity associated with the sensitive information.

4. The method of claim 3, wherein the blockchain database further includes information from the entity systems pertaining to actions involving the served entity, and the method further comprises:
    applying a set of rules specifying acceptable actions in the blockchain database to validate requested actions involving the served entity.

5. The method of claim 4, wherein the applying of the set of rules further comprises:
    honoring a communication request and recording the communication request in the blockchain database when the set of rules is not violated.

6. The method of claim 1, wherein the served entities include patients, and the entity systems include healthcare systems.

7. The method of claim 1, further comprising:
    updating the determined entity systems in response to additional data being received within a new block added to the blockchain database.

8. A first entity system for exchanging sensitive information among a plurality of entity systems, the first entity system comprising:
    at least one processor; and
    at least one memory connected to the at least one processor, wherein the at least one processor is configured to perform:
        applying a hash function to a portion of sensitive information of the first entity system to produce hash values;
        storing transaction information pertaining to transactions performed on the first entity system within a blockchain database accessible to the plurality of entity systems, wherein the transaction information includes the hash values for the portion of the sensitive information, and wherein the blockchain database includes transaction information from the plurality of entity systems including hash values from others of the plurality of entity systems;
        comparing the hash values of the first entity system to the hash values from the others of the plurality of entity systems to determine entity systems containing information pertaining to one or more common served entities; and exchanging the sensitive information for the one or more common served entities of the first entity system with the determined entity systems containing information for those one or more common served entities.

9. The first entity system of claim 8, wherein the blockchain database further includes encryption parameters for encrypting data to be sent to the plurality of entity systems, and the exchanging the sensitive information comprises:

encrypting the sensitive information for the one or more common served entities utilizing the encryption parameters of each of the determined entity systems within the blockchain database, wherein the encryption parameters for a corresponding entity system are associated with a private key limiting decryption to that corresponding entity system; and transmitting the encrypted sensitive information to each of the determined entity systems for decryption via the associated private key.

10. The first entity system of claim 9, wherein the at least one processor is further configured to perform:

analyzing the exchanged sensitive information to identify one or more issues triggering an action involving a served entity associated with the sensitive information.

11. The first entity system of claim 10, wherein the blockchain database further includes information from the entity systems pertaining to actions involving the served entity, and the at least one processor is further configured to perform:

applying a set of rules specifying acceptable actions in the blockchain database to validate requested actions involving the served entity.

12. The first entity system of claim 11, wherein the applying of the set of rules further comprises:

honoring a communication request and recording the communication request in the blockchain database when the set of rules is not violated.

13. The first entity system of claim 8, wherein the served entities include patients, and the entity systems include healthcare systems.

14. The first entity system of claim 8, wherein the at least one processor is further configured to perform:

updating the determined entity systems in response to additional data being received within a new block added to the blockchain database.

15. A computer program product comprising:

at least one computer readable storage medium having computer readable program code embodied therewith for execution on at least one processor, the computer readable program code being configured to be executed by the at least one processor to perform:

applying a hash function to a portion of sensitive information for each entity of a first entity system to produce hash values;

storing transaction information pertaining to transactions performed on the first entity system within a blockchain database accessible to the plurality of entity systems, wherein the transaction information includes the hash values for the portion of the sensitive information, and wherein the blockchain database includes transaction information from the plurality of entity systems including hash values from others of the plurality of entity systems;

comparing the hash values of the first entity system to the hash values from the others of the plurality of entity systems to determine entity systems containing information pertaining to one or more common served entities; and exchanging the sensitive information for the one or more common served entities of the first entity system with the determined entity systems containing information for those one or more common served entities.

16. The computer program product of claim 15, wherein the blockchain database further includes encryption parameters for encrypting data to be sent to the plurality of entity systems, and the exchanging the sensitive information comprises:

encrypting the sensitive information of the one or more common served entities utilizing the encryption parameters of each of the determined entity systems within the blockchain database, wherein the encryption parameters for a corresponding entity system are associated with a private key limiting decryption to that corresponding entity system; and transmitting the encrypted sensitive information to each of the determined entity systems for decryption via the associated private key.

17. The computer program product of claim 16, wherein the computer readable program code is further configured to be executed by the at least one processor to perform:

analyzing the exchanged sensitive information to identify one or more issues triggering an action involving a served entity associated with the sensitive information.

18. The computer program product of claim 17, wherein the blockchain database further includes information from the entity systems pertaining to actions involving the served entity, and the computer readable program code is further configured to be executed by the at least one processor to perform:

applying a set of rules specifying acceptable actions in the blockchain database to validate requested actions involving the served entity.

19. The computer program product of claim 18, wherein the applying of the set of rules further comprises:

honoring a communication request and recording the communication request in the blockchain database when the set of rules is not violated.

20. The computer program product of claim 15, wherein:
the served entities include patients, and the entity systems include healthcare systems.

21. The computer program product of claim 20, wherein the computer readable program code is further configured to be executed by the at least one processor to perform:

updating the determined entity systems in response to additional data being received within a new block added to the blockchain database.

* * * * *